(12) United States Patent
Lefcourt et al.

(10) Patent No.: US 7,547,508 B1
(45) Date of Patent: Jun. 16, 2009

(54) USE OF NANOSECOND SCALE, TIME-RESOLVED, IMAGING TO DIFFERENTIATE CONTEMPORANEOUS FLUORESCENCE RESPONSES FROM MULTIPLE SUBSTANCES

(75) Inventors: Alan M. Lefcourt, Elkridge, MD (US); Moon S. Kim, Silver Spring, MD (US); Yud-Ren Chen, Laurel, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 430 days.

(21) Appl. No.: 11/304,381

(22) Filed: Dec. 15, 2005

Related U.S. Application Data

(60) Provisional application No. 60/640,340, filed on Dec. 30, 2004.

(51) Int. Cl.
*C12Q 1/00* (2006.01)
(52) U.S. Cl. ............................... 435/4; 435/34; 435/29; 356/317
(58) Field of Classification Search ..................... 345/4
See application file for complete search history.

(56) References Cited

U.S. PATENT DOCUMENTS

| | | | |
|---|---|---|---|
| 5,474,910 | A | 12/1995 | Alfano |
| 5,621,215 | A | 4/1997 | Waldroup et al. |
| 5,914,247 | A | 6/1999 | Casey et al. |

OTHER PUBLICATIONS

Mehl et al., Development of hyperspectral imaging technique for the detection of apple surface defects and contaminations, Journal of Food Engineering, vol. 61, 2004, p. 67-81.*
Kim, Moon S., et al., "Uses of Hyperspectral and Multispectral Laster Induced Flourescence Imaging Techniques for Food Safety Inspection", Key Engineering Materials, vols. 270-273, pp. 1055-1063, 2004.
Kim, Moon S., et al., "Optimal Fluorescence Excitation and Emission Bands for Detection of Fecal Contamination", Journal of Food Protection, vol. 66, No. 7, 2003, pp. 1198-1207.
Kim, Moon S., et al., "Multispectral Laster Induced Fluorescence Imaging System for Large Biological Samples", Applied Optics, vol. 42., No. 19, Jul. 1, 2003.
Lefcourt, Alan M., et al., "Automated Detection of Fecal Contamination of Apples by Multispectral Laster-Induced Fluorescence Imaging", Applied Optics, vol. 42, No. 19, Jul. 1, 2003.
Kim, M.S., et al., "Multispectral Detection of Fecal Contamination on Apples Based On Hyperspectral Imagery: Part II. Application of Hyperspectral Fluorescence Imaging", Transactions of the ASAE, VI 45(6), pp. 2039-2047, 2002.
Kim, Moon S., et al., "Automated Detection of Fecal Contamination of Apples Based on Multispectral Fluorescence Image Fusion", Journal o f Food Engineering, 71 (2005), pp. 85-91.

* cited by examiner

*Primary Examiner*—Jon P Weber
*Assistant Examiner*—Tiffany M Gough
(74) *Attorney, Agent, or Firm*—John Fado; Randall E. Deck; Lesley Shaw

(57) ABSTRACT

Time-dependent differences in fluorescence responses of normal surfaces of the fruit or vegetable as opposed to surfaces which are contaminated with feces, may be used for improved detection of feces-contaminated fruits and vegetables. In this process, the surface of a fruit or vegetable which contains a native chlorophyll is illuminated with a pulse of UV or visible light having a wavelength effective to elicit fluorescence of feces of a plant consuming animal. The intensity of fluorescent light emissions from the surface are measured at one or more wavelengths characteristic of the emission spectra of chlorophyll or its degradation products, at a nanosecond-scale time period or window which is after the peak emission of the native chlorophyll of the fruit or vegetable. The presence of fecal contamination is determined by comparing this measured intensity to a threshold value of the intensity of fluorescent light emissions for a non-feces contaminated control of the same fruit or vegetable measured at substantially the same conditions, substantially the same said time period, and at substantially the same said wavelengths. A determination that the measured intensity of the fluorescent light emissions is significantly greater than the threshold value is an indication of the presence of fecal material on the surface of the fruit or vegetable.

19 Claims, 2 Drawing Sheets

USE OF NANOSECOND SCALE, TIME-RESOLVED, IMAGING TO DIFFERENTIATE CONTEMPORANEOUS FLUORESCENCE RESPONSES FROM MULTIPLE SUBSTANCES

This application hereby claims the benefit of U.S. provisional patent application 60/640,340, filed Dec. 30, 2004, the content of which are incorporated by reference herein.

BACKGROUND OF THE INVENTION

1. Field of the Invention

The invention relates to an improved method and apparatus for detecting fecal contamination on the surface of produce using visible light fluorescent spectroscopy.

2. Description of the Prior Art

Microbial pathogens in food cause an estimated 6.5 million to 33 million cases of human illness and up to 9,000 deaths annually, according to the Council for Agricultural Science and Technology. Furthermore, the USDA Economic Research Service has recently reported that the annual cost of the food borne illnesses caused by six common bacterial pathogens, *Campylobacter* spp., *Clostridium perfringens*, *Escherichia coli* O157:H7, *Listeria monocytogenes*, *Salmonella* spp., and *Staphylococcus aureus*, ranges from 2.9 billion to 6.7 billion dollars (Food Institute Report, USDA, AER, December, 1996).

Feces are the primary source of pathogenic *E. coli* contamination of agricultural commodities, and both FDA[1] and FSIS[2] use the presence of *E. coli* as an indicator of fecal contamination. The adverse health risks of pathogenic organisms originating from feces, including *E. coli* O157:H7, in foods are well documented.[3-7]

Although the foods most typically associated with these illnesses are animal products such as red meat, poultry and eggs, seafood, and dairy products, fruits and vegetables, and particularly apples used to make juice, have faced increased scrutiny as potential sources of illness for consumers. For example, fruits and vegetables are commonly contaminated with fecal material during the spreading of manure.

Fluorescence sensing techniques are widely used in a number of scientific applications including cell biology, photochemistry, medicine, and environmental sciences.[8-11] Plant materials including leaves and fruits exhibit fluorescence emissions in the visible (VIS) region of the spectrum when excited with appropriate radiation.[12-15] Fluorescence emission peaks (maxima) from these materials are typically observed in the blue, green, red, and far-red regions of the spectrum at approximately 450, 530, 685, and 735 nm, respectively. We have demonstrated that feces show similar responses, and that responses from feces from different species of agricultural interest are similar.[16]

In prior studies, we have demonstrated that fecal contamination of apples can be detected based on differential fluorescence responses of feces and normal apple surfaces.[13,17] We have developed a multispectral laser-induced fluorescence imaging system, which has been used to detect fecal contamination of apples.[17,18] The system used a UV pulsed laser to excite samples and an intensified camera to record fluorescence responses. A specific advantage of this pulsed-laser system is that images from samples with low quantum yields can be acquired very rapidly regardless of ambient light conditions.

However, despite these advances, there remains a continuing need for a high-speed system capable of detecting feces on fruits and vegetables in real-time during processing.

SUMMARY OF THE INVENTION

We have now invented a novel and improved method for detecting fecal contamination on the surface of fruits and vegetables. We have discovered that time-dependent differences in fluorescence responses of normal surfaces of the fruit or vegetable as opposed to surfaces which are contaminated with feces, may be used for improved detection of contaminated fruits and vegetables. In this process, the surface of a fruit or vegetable which contains a native chlorophyll is illuminated with a pulse of UV or visible light having a wavelength effective to elicit fluorescence of feces of a plant consuming animal. The intensity of fluorescent light emissions from the surface are measured at one or more wavelengths characteristic of the emission spectra of chlorophyll and its degradation products, at a nanosecond (ns)-scale time period or window which is after the peak emission in time scale of the native chlorophyll of the fruit or vegetable. The presence of fecal contamination can be determined by comparing this measured intensity to a threshold value of the intensity of fluorescent light emissions for a non-feces contaminated control of the same fruit or vegetable measured at substantially the same conditions, substantially the same said time period, and at substantially the same said wavelengths. A determination that the measured intensity of the fluorescent light emissions is significantly greater than the threshold value is an indication of the presence of fecal material on the surface of the fruit or vegetable.

In accordance with this discovery, it is an object of this invention to provide an improved method for detecting the presence of fecal contamination on the surface of fruits or vegetables to improve the safety of the food supply.

Another object of the invention is to provide an improved high-speed method which is capable of near real-time detection of fecal contamination on the surface of fruits and vegetables, which would not interfere with existing commercial processing or handling procedures.

Yet another object of the invention is to provide an improved method and apparatus which for the detection of fecal contamination on the surface of fruits or vegetables utilizing time-dependent differentiation of the fluorescence responses of chlorophyll in feces and native, chlorophyll in the fruit or vegetable.

Other objects and advantages of the invention will become apparent from the ensuing description.

DETAILED DESCRIPTION OF THE INVENTION

Figure 1:
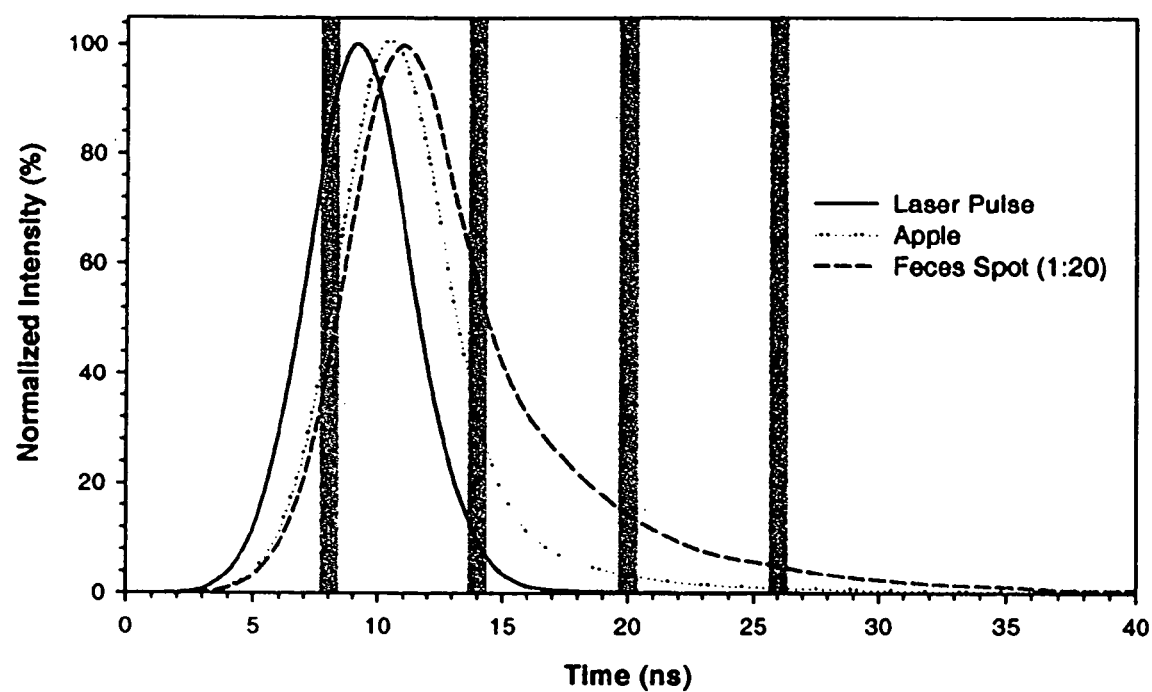
FIG. 1 is a normalized fluorescence decay curve of apple and 1:20 feces treated spots representative of those in Example 1. The laser excitation pulse is also shown.

The process of this invention may be used for detecting the feces from any animal which directly or indirectly consumes plant material, which feces is present as a contaminant on the surface of fruits or vegetables, particularly during post-harvest commercial processing. While the invention may be used for the detection of feces on the surface of a variety of fruits and vegetables, it is of particular value for the detection of feces on the surface of pome fruits, stone fruits, lettuce, melons, berries, and greens, most particularly apples, pears, iceberg lettuce, romaine lettuce, cantaloupe, strawberries, collard greens, and spinach. Fruits and vegetables which may be tested include those intended for sale as whole or cut fresh produce, as well as that destined for further processing such as, but not limited to apples or other fruits and vegetables intended for juice. In a preferred embodiment, the fruits and vegetables will be tested as they conveyed in a packing plant or a processing plant. However, it is also envisioned that they may be tested in the field as the fruit or vegetables are harvested such as during an automated or semi-automated mechanical harvesting.

Detection of feces on fruits and vegetables in accordance with this invention is based upon applicants' discovery that the fluorescence responses of the surface of fruits and vegetables exhibit ns scale time-dependent differences from the fluorescence responses of feces of plant-eating animals. Specifically, the fluorescence responses of the chlorophyll contained in intact and healthy fruits and vegetables exhibit time-dependent differences from the fluorescence responses of chlorophyll and its degradation products contained in the feces. Moreover, the fluorescence responses of the surface may be differentiated from the fluorescence response of the feces by measurement of the fluorescence responses at a specific, nanosecond-scale time window.

Traditional methodologies have dictated that the kinetic responses of the molecules' fluorescence emissions be measured over the entire fluorescence time decay curve. While accurate in most of the cases, such methodologies are prone to failure for detection of fecal contamination when the fluorescence responses or intensities of the fruits and vegetables are similar to the feces on the surfaces of fruits and vegetables. However, in accordance with the process of the invention, the fruits and vegetables and animal feces exhibited different ns scale time dependent fluorescence decay characteristics, and thus fecal contamination can be detected by means of selecting a ns time-scale window where the most significant difference occurs between the fruits and vegetables and the feces on the surfaces of fruits and vegetables, in as little as a single, nanosecond-scale time period or window of the time decay curve.

In practice, the surface of the fruit or vegetable to be examined for contamination is illuminated with a pulse of either UV or visible light having one or more wavelengths which are effective to elicit fluorescence of the feces of a plant consuming animal. The actual excitation wavelength selected is not critical, and a wide range of wavelengths are suitable for use herein. However, to simplify the subsequent measurement of fluorescence and eliminate any contribution from the illuminating light source, the wavelength of the excitation light less than the measured fluorescence wavelengths. Without being limited thereto, suitable wavelengths of excitation light are between about 280 to 670 nm, preferably between about 410 to 430 nm. The duration of the pulse of the illuminating light is preferably short, less than about 20 ns, most preferably less than about 10 nanoseconds.

After illumination, ns-scale time dependent fluorescent light emissions from the surface of the fruit or vegetable are measured at one or more wavelengths which are characteristic of the emission spectra of chlorophyll, particularly chlorophyll a, and its degradation products. As used herein, "wavelengths which are characteristic of the emission spectra of chlorophyll and its degradation products" are defined herein as the one or more wavelengths exhibiting measurable fluorescence in the fluorescence spectrum of chlorophyll and its degradation products (when illuminated with light at the same, selected excitation wavelength). A variety of wavelengths are suitable for measurement of the fluorescence emissions, and the optimal wavelengths will vary somewhat with the animal source of the suspected feces, and the particular fruit or vegetable being examined. By way of example, suitable emission wavelengths include but are not limited to between about 550 nm to about 760 nm, preferably between about 600 nm to about 760 nm, most preferably wavelengths centered at about 590 nm (between about 550 nm to about 630 nm), about 630 nm (between about 610 nm to about 650 nm), about 670 nm (between about 650 nm to about 700 nm), about 700 nm (between about 670 nm to about 730 nm), and about 730 nm (between about 720 nm to about 740 nm). In general, detection of fluorescence centered at about 660 nm to about 670 nm is preferred for detection of feces from any plant consuming animal.

As noted above, the fluorescent light emissions from the surface of the fruit or vegetable are measured within a nanosecond-scale time period or window of the time decay curve. Specifically, the intensity of fluorescent light emissions from the surface are measured at a time period which is after the peak emission intensity in time-scale of the native chlorophyll of said fruit or vegetable (measured at the same emission wavelength). In accordance with this method, the intensity of fluorescence of chlorophyll in any contaminating feces can be differentiated from native chlorophyll contained in the fruit or vegetable. In general the time period is preferably after the peak emission of the native chlorophyll of the fruit or vegetable, and after the time at which at least about 50% of the energy of the fluorescent light emissions at the selected wavelength has dissipated as measured in a fluorescence time decay curve (such as shown in FIG. 1). However, it is also envisioned that the time period may be after the peak emission of the native chlorophyll of the fruit or vegetable, but before the time at which about 50% of the energy of the fluorescent light emissions at the selected wavelength has dissipated as measured in the fluorescence time decay curve. Without being limited thereto, in a preferred embodiment, the time period which is within about 50 nanoseconds after the peak emission of the native chlorophyll of the fruit or vegetable, more preferably between about 5 nanoseconds and about 50 nanoseconds after the peak emission of the native chlorophyll of the fruit or vegetable.

Following measurement of the ns-scale time dependent fluorescent light emissions, the intensity of the measured emissions can be compared to a threshold value of the intensity of fluorescent light emissions for a non-feces contaminated control of the same fruit or vegetable measured at substantially the same conditions, substantially the same said time period, and at substantially the same said wavelengths. The determination that the intensity of said fluorescent light emissions measured from the surface of the test fruit or vegetable is significantly greater than this threshold value is a presumptive positive indication of the presence of fecal material on the surface of the fruit or vegetable. In brief, the fluorescence decay curve for a normal, non-contaminated fruit or vegetable (in this case an apple) exhibits a time dependent emission which peaks before the feces. As described in greater detail hereinbelow, these decay curves can be used to set a threshold which can be used to differentiate the contaminated from non-contaminated surfaces. Because the value of the threshold may be measured or predetermined, the detection of fluorescence at an intensity greater than this threshold is a presumptive indication of fecal contamination.

The precise value of the threshold will of course vary with the selected time period, the particular fruit or vegetable being examined, and the desired level of selectivity, and may be readily determined by the user by routine experimentation. Moreover, a practitioner skilled in the art will recognize that there are a variety of detection methods that can be used to generate a statistically effective threshold. Suitable methods may include, but are not limited to selection by the user based upon a subjective assessment of an image, normalization of an image, and determination of localized thresholds. In a first preferred embodiment, this threshold value is a fixed value, which is predetermined by measurement of the intensity of the fluorescent light emissions from a healthy, non-contaminated control sample of the same fruit or vegetable measured at the same conditions, time period, and wavelengths as the subsequent test fruits or vegetables. However, although this embodiment provides the simplest method for determining the threshold and requires relatively low computing power, the sensitivity may be reduced due to variations between individual pieces of the subject fruit or vegetable. In a second preferred embodiment, sensitivity may be increased, albeit at the expense of an increase in required computing power and computation time. In this second embodiment, because it can be reasonably expected that pieces of fruits and vegetables will rarely be completely covered with feces in the field, the value of the threshold may be determined for each piece of fruit or vegetable tested "on-the fly", by examining a non-contaminated region of the fruit or vegetable. A variety of techniques or algorithms may be used for finding a non-contaminated region from where the threshold value of the intensity can be obtained. For example, if it is assumed that less than 50% of any given piece of fruit or vegetable will be covered with feces, then the intensity of the fluorescence can me measured at a plurality of positions thereon, and the median value of these measurements may then be used to select the threshold "on the fly." In addition, standard gradient transformations, such as edge detection algorithms, can be used to enhance images prior to determination of a threshold.

In an alternative embodiment, the intensity of the fluorescent light emissions may be measured at least two of the above-described wavelengths and the ratios of these intensities determined (with the threshold value being similarly determined as a ratio at the same wavelengths). As described in greater detail in the examples, for some fruits and vegetables such as golden delicious apples, the determination of such ratios may help to normalize effects due to heterogeneous illumination and improve detection of fecal contamination. However, the use of ratios is optional and may not be beneficial for all fruits and vegetables. The selection of the optimal wavelengths for use in determining the ratios may be determined by the skilled practitioner by routine experimentation as described in the examples, and the skilled practitioner will recognize that there are a variety of techniques to maximize the statistical difference between the ratios.

The process of the invention described above can provide an accurate indication of the presence of fecal contamination at the location on the surface of the fruit or vegetable from where the fluorescence emissions are measured. Thus, the analysis should be repeated at a plurality of locations across the surface being examined. In the preferred embodiment, this is effected by acquiring a digital or digitized image of the test fruit or vegetable, measuring the intensity of the fluorescent light emissions at each position (or pixel) and applying or subtracting the threshold value. In this embodiment, the presence and number of adjacent positions or pixels having intensities which are significantly greater than the threshold value may determined, and will provide an indication of the relative size of the site of fecal contamination.

In another alternative preferred embodiment, a binary classification image may be prepared, also as described by Lefcourt et al.[17] or Kim et al.[20], the contents of each of which are incorporated by reference herein. In this embodiment, the intensities at the selected wavelengths may be measured at each position or pixel and then compared to the threshold value. The measured intensity at each position which is less than this threshold is assigned a first color, such as black, while each intensity which is greater than the threshold is assigned a second, contrasting color, such as white. Intensities which are equal to the threshold value may be assigned to either color depending upon the desired selectivity. A binary classification image may then be generated from these color values at their respective positions or pixels. In this image, fecal contamination will be shown as one color (such as white) while the non-contaminated healthy surface of the fruit or vegetable is shown by the other color (in this case, black).

Upon determination of the presence of fecal contamination, a number of responses may be initiated. For instance, the detection of fecal contamination may trigger one or more audible or visible signals alerting the appropriate production worker who may then manually remove the offending fruit or vegetable from the conveyor line. However, in the preferred embodiment, any fruit or vegetable determined to be contaminated with feces may be automatically removed from the production line. The fruit or vegetable may be discarded, or it may be washed, disinfected or otherwise treated to remove the feces from the surface thereof. The process for detecting feces on the washed surface is then repeated, followed by additional washing and/or disinfection steps if necessary, until all traces of feces have been removed or destroyed. A variety of wash solutions or disinfectants are known in the art and are suitable for use herein and include but are not limited to pressurized water or steam sprays, organic acids, chlorinated water, hypochlorous acid, detergents, and treatment with radiation. Once the fruit or vegetable has been determined to be free of contamination, it may be subjected to further processing or shipped.

The apparatus for measuring the fluorescence emissions is not critical. However, in a preferred embodiment, a multispectral laser-induced fluorescence imaging system (MLIFIS) is used, such as described in Kim et al.[13] and Kim et al.[18], the contents of each of which are incorporated by reference herein. This system incorporates pulsed lasers with a short pulse duration and a fast-gated detection system synchronized to the laser pulses to allow capture of the fluorescent light emissions in ambient light. Moreover, this system also allows the simultaneous acquisition of multispectral images, currently at 4 different wavelengths, including the desired first and second wavelengths. Thus, up to six different ratios could be determined simultaneously. In brief, the MLIFIS includes a pulse laser as the illumination source, a beam expander, a lens, a common-aperture adapter, and a fast-gated intensified camera. A microprocessor based control unit having conventional interface hardware may be provided for receiving and interpreting the signals from the camera, and manipulating data and/or generating images as described above. An audible or visible signal generator may be provided in communication with the microprocessor, and the microprocessor may also be used for automated control of testing, including automated scanning of samples on a conveyor line, identifying samples positive for fecal contamination, and directing the same from the conveyor line.

The following examples are intended only to further illustrate the invention and are not intended to limit the scope of the invention which is defined by the claims.

EXAMPLE 1

1. Introduction

This example describes the method of using a laser-induced fluorescence imaging system for detecting fecal contamination on apples. We have previously shown that the maximal fluorescence yield from feces is obtained using an excitation wavelength around 417 nm.[16] In this study, the UV pulsed-laser was replaced by a pulsed-laser with an output wavelength of 417 nm. In addition, we hypothesized that consideration of time-dependent differences in fluorescence responses of areas with or without feces treatment might allow for improved detection of contaminated apples. To test this possibility, an intensified camera with a gate-width of two ns was used to image artificially contaminated apples sequentially by time.

2. Materials and Methods

Serial dilutions of dairy feces were applied to Red Delicious and Golden Delicious apples. Contamination sites were detected by taking advantage of differences between fluorescence responses of apple surfaces and of feces on apple surfaces. One-half of the apples were used to develop detection algorithms. The algorithms were validated using the remaining apples.

A. Apples

The Red Delicious and Golden Delicious apples used in the study were handpicked from crates of tree-run apples at the Rice Fruit Co. (Gardners, Pa.). The apples were stored under commercial conditions in an apple refrigerator maintained at 3° C. Apples for treatment were selected randomly based on two criteria: that the apples were not damaged and second that the flesh of the apple was firm with no sign of rot. Feces were applied to 100 apples of each type.

B. Feces Application

Fresh cow feces were collected at the Beltsville Agricultural Research Center dairy. The feces was immediately processed and applied to the apples. Dry-matter content of the feces (14.8±0.2%) was determined by drying three samples to a constant weight in a 95° C. oven. The fresh feces were serially diluted 1:2, 1:20, and 1:200 by weight with double-distilled water. A single 30 µl drop of each of the three dilutions was applied to the cheek surface of individual apples using a pipette with one drop per quadrant; the fourth quadrant was not treated. To accommodate particulates in the dilutions, about 2 mm was cut-off of the end of the pipette tip using a razor blade. The drops were applied clockwise in sequence by concentration and the initial quadrant for application was rotated one quadrant clockwise every fourth apple.

The last four apples in each group of 100 were handled a little differently than the remainder of the apples. The locations of specific treatment sites on these four apples were rotated apple by apple so that the four application patterns were all represented. These four apples were designed to be potential substitutes if problems occurred with any of the other 96 apples. In actuality, two Red Delicious apples were substituted because one was dropped and because one application site visibly ran, and one Golden Delicious apple was substituted because the application pattern was rotated inappropriately. Thus, only 96 apples from each group were actually used for analyses.

Following feces application, the apples were returned to the apple refrigerator. Over the next 24- to 72 h, single trays of a dozen apples were removed for imaging as needed. Two trays were out of the refrigerator at any given time, one tray was in active use while the apples in the second tray were allowed to acclimate to room temperature.

C. Imaging System

Fluorescence emissions from single apples were acquired using a multispectral laser induced fluorescence imaging system. The light source was a 10 Hz pulsed laser with an approximately 6 ns pulse width. Trials were conducted using 417 nm excitation at a power level of 25 to 30 mj per pulse. A pair of internal lenses expands the beam of the laser to encompass a 12 cm diameter target area at 150 cm. A Gen IV ICCD camera was used for imaging (IStar; Andor Technology, MA; minimum gate width 2 ns, pixel resolution 1024×1024, and effective pixel size 13 $\mu m^2$). Attached to the camera was a 25 mm Nikon lens along with a common-aperture multispectral adaptor (MSAI-04; Optical Insights, AZ) that uses prisms to create four 512×512 images in separate quadrants of the 1024×1024 camera image. The advantage of this adapter is that a different interference filter can be used for each quadrant. Filter parameters used for this study were: 40 nm FWHM at 590 nm (yellow band), 22 nm FWHM at 678 nm (red band), 30 nm FWHM at 700 nm (broad red band), and 10 nm FWHM at 730 nm (far-red band). The camera was positioned at a 5° angle to the laser beam at a distance from the target stage (~100 cm) to allow single apples to be imaged. Preliminary tests of imaging quality indicated that the largest source of variation was the fluorescence responses across individual, untreated, apple surfaces and among apples. Second was the variability inherent in using a pulsed laser for illumination; however, averaging responses of eight sequential pulses kept differences in image-to-image illumination to less than 2%. Tests of optical components revealed distinct optical aberrations due to the multispectral adapter at the edges of each of the four imaging quadrants. However, within the center regions used to image apples, responses were near uniform. In practice, no attempt was made to correct images prior to image analyses. The primary reason for this decision was that the variability that can be attributed to the imaging system is minimal and, as the ultimate goal of the research is the development of a very rapid detection system, the computational overhead of an additional correction step is not warranted.

D. Image Acquisition

The camera is controlled, and data are collected and analyzed using a PC running Microsoft Windows XP PROFESSIONAL (Microsoft Corp., Redmond, Wash.) and VISUAL BASIC VERSION 6 (Microsoft Corp., Redmond, Wash.). Image acquisition uses the software development kit provided by Andor Technology to set the trigger delay time (ps), hardware binning (normally none), CCD temperature (normally −20° C.), intensifier gain (0 to 255), gate-width (ps), 16-bit A-to-D conversion rate (normally set to 500K Hz so that only one of the two existing A-to-D circuits is used for all conversions) and the number of images to accumulate, and to transfer individual images to digital arrays. Images are accumulated by leaving the CCD on and continuing to accumulate charge in individual pixel wells while the intensifier is turned on and off in relation to the Q-switch-based trigger and camera settings. A computer program was written to set the ROI (not used in this study), control image acquisition and display, and to write 15-bit images to disk. Images were restricted to 15-bit to allow data to be stored as signed integers. For most trials, a set of 30 images were acquired and saved to disk following activation of a single command button. For the first 28 images, the gain was 250, the gate-width was 2 ns, and the number of images accumulated was eight. The difference among images was that the trigger delay was incremented 1 ns for each sequential image. The initial trigger delay was set to a fixed value that corresponded to 3 ns before the first sign of a fluorescence response could normally be detected. For the 29th image (Low Range), the gate width was set to 25 ns, the gate delay was set to be the same as the 3rd sequential image, and the number of images accumulated was reduced from eight to six to maintain consistent intensity levels; the image is comparable to integrating sequential images 3 to 27. For the 30th image (High Range), the gate width was set to 20 ns, the gate delay was set to be the same as the 15th sequential image, and the number of images accumulated was again set to eight; the image is comparable to integrating sequential images 15 to 34. In actuality, only 28 sequential images were acquired so the final (High Range) image contains information not available in the sequential images. In a preliminary tests, images of treated apples acquired sequentially over 10 min periods showed no evidence of photobleaching.

E. Image Manipulation

A number of computer programs were written to facilitate analyses of images. The first program combined sets of images from 12 apples into a single 3-D "tray" file where the data were arranged as 2 apples by 6 apples by 30 images per apple. This program also allows creation of a file that contains location masks for each of the contamination sites. Because the image coordinates are identical for each of the 30 z-dimension images, the location file is two-dimensional and encompasses only the 2 apple by 6 apple dimensions of the tray files. The masks consisted of fixed-dimension squares that are manually positioned so that the selected contamination site is centered in the square. Type of contamination site is coded by color. The underlying image on which the squares are placed can be any one of the 30 z-dimension images, and the validity of location masks can be tested by superimposing the mask file on different z-dimension images. Larger masks were used to establish the exact location of apples within images.

Because of memory considerations, separate tray files were created for each of the four quadrants of the camera images, i.e. for each filter wavelength. The images in tray files were registered so that it was necessary to create only a single location file for each set of four related tray files. A second program allowed creation of combined 3-D image files based on tray and location files created by the first program. As each tray file contains images of 12 apples, eight tray files were needed to encompass images of the 96 apples of each type. To allow half the data to be used to develop algorithms and the other half to be used for validity testing, combined image files were created using apple masks and either odd or even numbered tray files. Thus, combined image files included images from 48 apples arranged as 8 apples by 6 apples; individual apple image segments were 351 by 351 pixels and masks for contamination sites were 25 by 25 pixels.

As the original combined image files contained information based on only a single filter, a program was written to expand the z-dimension from 30 to 32. The additional space allows inclusion of images, or transformed images, acquired using any filter. As the images are registered, the addition information allows manipulations such as taking ratios of images acquired using different filters.

F. Image Analyses

A fourth program was written to analyze the combined image files. An image derived from a segment of the combined image based on the mask used to create the combined image, e.g. a single apple image, can be analyzed using image manipulations (e.g., binning, brightness, contrast, normalization, exponential scaling, linear combination of images, and ratios of two images) and filters (e.g., spatial, geometric, morphological, edge, and threshold).[19] Raw or transformed images can be viewed as images, false color images, or histograms. Automated detection is accomplished by subjecting an image to a selected series of transformations, and then applying a threshold to the resultant image. All pixels above the threshold and within a selected pixel distance of each other are considered as to be from the same site. Classification of sites by treatment is accomplished by comparing the centroids of the sites with the centroids of the contamination site masks. A positive match occurs if the centroids are within a selected distance of each other. If enabled, the program records the centroid coordinates and the number of pixels associated with each classified contamination site along with similar information for the largest unclassified, presumably false-positive, site.

A final program tabulates recorded results. The numbers of recorded pixels for each classified contamination site and for the largest unclassified site are compared to a selected classification threshold. If the number of pixels is greater than or equal to the classification threshold, the response is tabulated as a true response. One option is to investigate the affect of changing the classification threshold on the number of contamination sites correctly detected verses the number of false positive sites detected. For example, all false positives for a particular detection algorithm can be eliminated by setting the classification threshold just greater than the largest number of detected pixels for any unclassified contamination site.

3. Results and Discussion

A. Response Characteristics

As was found in a prior study, the intensity of fluorescence responses did not scale with the concentration of applied feces.[17] The measured response for a treated area appears to be a weighted summation of the responses of the feces and of the underlying apple surface. The applied feces can obstruct illumination of the underlying apple surface and potentially reabsorb energy released by the apple surface. In general, the intensity of fluorescence responses in the red bands for 1:2 treatment areas was less than responses for 1:20 treatment areas. For the 1:2 dilution areas, the density of the applied manure probably interfered with both the illumination and response of the underlying apple surface. For the 1:20 dilution, the applied feces visually appeared to be translucent, and the measured response is probably a summation of the responses of the feces and the underlying apple surface. Given the complexity of these interactions, formal analyses of decay characteristics are beyond the scope of this study. Furthermore, information about theoretical decay characteristics is of little use for designing a commercial detection system as time and cost constraints do not allow for acquisition of sequential images for single apples. For commercial applications, it is more important to look at the relative intensity of responses as a function of potential gate widths and gate delays. For this reason, raw intensity responses by time are shown rather than normalized responses, which would be more appropriate for analyzing decay constants.

B. Detection Parameters

Selection of the wavelengths and bandwidths for filters used in this study was based on demonstrated fluorescence response characteristics of feces and apples. Using hyperspectral imaging techniques, the authors previously demonstrated that ratios of appropriate band images helped to normalize effects due to heterogeneous illumination and that detection of fecal contamination was enhanced when a red-band image was divided by the corresponding blue-band, and to a lesser extent green-band, image.[13] More recently, ratios of red-band to blue-band images acquired using a pulsed UV laser for excitation were found to improve detection of 1:2 dilutions of feces applied to Red Delicious apples; in contrast, detection of 1:200 dilution sites was better when only red-band images were analyzed.[17] In the current study, use of 417 nm excitation precluded use of a blue (~450 nm) filter. Instead, a broad-bandwidth 590 nm (yellow) filter was used to capture the tail-end of the green fluorescence emission spectra. The green coloration of Golden Delicious apples resulted in higher intensity fluorescence responses in the yellow-band for untreated apple surfaces compared to Red Delicious apples. As a consequence, for Golden Delicious apples, fluorescence responses in treated areas were lower than responses in untreated areas. In contrast, for Red Delicious apples, responses for 1:2 dilution treatment sites were greater than responses for untreated areas. The responses of 1:2 dilution treatments are of particular interest as ratio images are most beneficial for detecting high concentration treatment sites.[17] Ratio images enhance differences between treated and untreated areas when the direction of the relative response of treated to untreated areas in one image is reversed in the second image. Thus, ratio images utilizing 590 nm images offer the potential of enhancing detection of fecal contamination on Golden Delicious, but not on Red Delicious apples.

Figure 2:
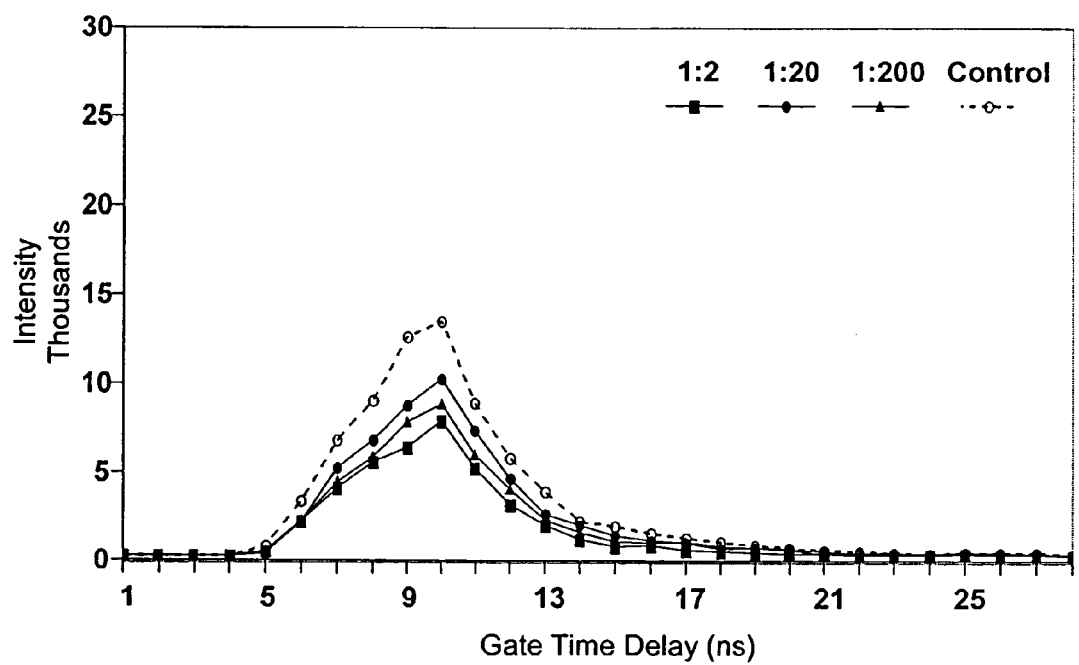
FIG. 2 shows the average intensities of 9×9 pixel areas for treatment spots on the (a) Red Delicious and (b) Golden Delicious, respectively. Calculated intensities were derived from images acquired using gate delay times incremented sequentially by 1 ns; gate width was kept constant at 2 ns. Note that for both (a) Red Delicious and (b) Golden Delicious apples, at 10 ns gate delay intensities for 1:2 treatment areas are less than corresponding responses for control areas, and at gate delays greater than 10 ns intensities for 1:2 treatment areas are greater than corresponding responses for control surfaces.

The 682 nm filter was chosen for use, as it was the commercially available filter that best matched the primary fluorescence response characteristics of chlorophyll a. The 700 nm filter was meant to encompass both the primary and secondary chlorophyll a fluorescence emissions peaks. The intensity of responses of treated and untreated areas are shown in FIG. 2.

When using a multispectral adapter for imaging, an issue that needs to be addressed is the effective imaging throughput of each of the filters. A broad-band filter was used at 590 nm in an attempt to match the intensities of images acquired using the 682 and 700 nm filters. However, due to low fluorescence yields using 417 nm excitation, the intensity of images acquired using the 590 nm filter was lower than the intensity of images acquired using the 682 (FIG. 2) or 700 nm filters. Still, the throughput for the 590 filter was adequate to provide reasonable sensitivity as pixel counts for regions of interest ranged from one thousand to 20 thousand. The throughput for the narrow-band 730 nm was the lowest among all the filters, and pixel intensities for regions of interest ranged from the low hundreds to a few thousand. While this sensitivity is theoretically adequate to allow effective analyses of images, the images were very noisy and grainy. As 730 nm is the secondary emission peak of chlorophyll a, the 730 images were similar to the 682 and 700 nm images, but were inferior in terms of signal-to-noise ratio. For these reasons, 730 nm images were not subject to detailed analyses.

We hypothesized that consideration of differences in the time courses of fluorescence responses for treated and normal apple surfaces might allow for improved detection of feces on apples. The fluorescence responses of feces and of apples in the red-band are both derived from chlorophyll a and related compounds. However, feces are the result of a digestive process designed to breakdown biological tissue into simpler chemical compounds. We theorized that this process might alter the time-dependent fluorescence responses of feces compared to intact apples. If so, it might be possible to accentuate differences between corresponding fluorescence responses by using a pulsed laser for excitation with appropriate selection of the ICCD camera gate time delay and gate width. Images clearly demonstrated that the time courses of fluorescence responses of feces and of normal apple surfaces were different. Graphs of intensity verses gate time delay (FIG. 2) reveal that the fluorescence responses for normal apple surfaces decrease faster with elapsed time compared to areas treated with feces. In contrast, there were no real differences in time-dependent response characteristics at 590 nm.

The Low Range (3-to-27 ns gate window) and High Range ns gate window) imaging parameters were selected based on preliminary data. The Low Range was designed to capture the total integrated fluorescence response. The High Range was selected to capture the tail of the feces response after the response of untreated apple surface was greatly attenuated. Examination of experimental data suggested that the 12-to-19 ns gate window might also be worth investigating, as this is the range where responses of treated areas were consistently greater than responses for untreated areas. Images acquired with gate delay times of from 12 to 19 ns were averaged to create the Midrange treatment for testing.

Examination of time-sequence images show that towards the end of the response period for treated areas there was almost no response for untreated apple surfaces. Tests made using images acquired with gate delay times greater than 18 ns led to the creation of an additional treatment called the Extended Range treatment. For both Red Delicious and Golden Delicious apples the treatment was the sum of images acquired from 20 to 24 ns.

It is interesting to note that the shape of fluorescence responses were similar for both treated and untreated areas in images acquired using the 590 nm filter. Responses were largely attenuated by 13 ns. This presents a particular problem for constructing ratio image. Ratios involving High Range, and even Midrange, treatments are not very useful as there is little or no energy in corresponding images acquired using the 590 nm filter. As an alternative, images acquired with gate delay times of from 11 to 13 ns were averaged and designated the Short Range treatment. Ratios were calculated for Low Range and Short Range image sets.

In summary, images acquired using both 682 and 700 nm filters were analyzed in detail using the Low Range, Short Range, Midrange, High Range, and Extended Range image sets. In addition, ratio images for Low Range and Short Range data sets were also analyzed. The denominators for all ratio calculations were the corresponding image sets acquired using the 590 nm filter.

C. Detection Algorithms

Numerous detection algorithms were tested by applying the algorithms to 48 Red Delicious and 48 Golden Delicious apples. It immediately became apparent that it would be impossible to detect all of the contamination areas with no "false" positives. For both group of apples, a number of apples showed signs of natural "contamination." In most cases, there was no abnormality associated with the natural contamination sites that was visible to the naked eye. In a few cases, the response was associated with what appeared to be a healing wound. An additional clue concerning natural contamination sites is that apples with such sites had a tendency to show early signs of an infection process, including brown areas. However, the detected natural sites did not generally correspond to the potential disease sites. Of course, some of the natural contamination may actual be fecal contamination that occurred prior to harvesting or as a result of splatter during feces application.

Given the existence of the natural contamination sites, tradeoffs between detection of artificial and natural contamination sites became a critical issue. In general, the artificial sites were larger than the natural sites. However, if the classification threshold is increased to reduce the number of "false" positives, the minimum theoretical size of any contamination site that can be detected is increased. Also, raising the threshold too high will reduce the number of artificial contamination sites detected. To better determine the affect of the classification threshold on detecting natural and artificial contamination sites, the numbers of pixels above the threshold for natural sites were sorted from largest to smallest. Then the classification threshold was set sequentially to match these values. For example, if the classification threshold is set to the third largest value, the first two natural contamination sites will be classified as real responses. Empirically, the number of correctly classified artificial sites jumped upward when the threshold was set to match the fifth largest value for natural contamination sites. The natural contamination sites produce the second or third largest responses, depending on the detection algorithm used, and are always classified as a true response when the classification threshold is set to match the fifth largest pixel count for natural contamination sites.

The pixel count for the fifth largest natural contamination site for the detection algorithm being tested was selected to be the classification threshold for testing of detection algorithms. Although this threshold was derived empirically, the procedure used to select the threshold is reasonable and it allows direct comparison of different detection algorithms. In addition, the successful application of algorithms derived using the sets of apple test images to the validation image sets, as discussed below, demonstrates the appropriateness of using this methodology.

After numerous trials using the sets of test images, two types of algorithms were selected for further optimization. Both algorithms first transformed the images using a linear transform to equalize intensities; the 5 percent cumulative histogram level was mapped to an intensity of 20 and the 60 percent histogram level was mapped to an intensity of 100. The maximum intensity was limited to 1023. For the Extended Range image sets, a simple threshold was applied to the transformed images. The threshold was iterated until the maximum numbers of artificial contamination sites were detected, given that the classification thresholds were set to the pixel count of the fifth largest natural contamination site. For the other image sets, a 5×5 Prewitt filter[19] was applied to take advantage of the observation that contaminated areas were brighter than the surrounding untreated apple surface, regardless of variation in pixel intensities of untreated areas across an apple surface. The authors have previously demonstrated that edge detection can be a sensitive method for detecting fecal contamination on apples.[17] The only real problem with the use of edge detection is the tendency to detect the actual edges of the apple or small increases in pixel intensities at the edges of apples. To alleviate this problem, the minimum intensity of images was set just below the pixel intensity of apple edges prior to applying edge detection.

One additional step was necessary for analyzing ratio images. Registration of images was not perfect, which commonly resulted in enhanced detection of the actual edges of apples. To address this problem, the images used to calculate ratios were binned 2×2 prior to ratio calculations.

Detection results for Red Delicious and Golden Delicious apples are in tables 1 and 2, respectively. The optimized algorithms used to create tables 1 and 2 were applied to the second sets of apples without modification to test the validity and robustness of the optimized detection algorithms (Tables 3 and 4). The results for both sets of Red Delicious and for both sets of Golden Delicious apples were essentially identical, thus validating the methodology used to derive the detection algorithms.

For Red Delicious apples, the best overall image set for detection of artificial contamination sites was the Extended Range image set. However, only 40 of the 48 apples contaminated with the 1:2 dilution of feces was detected for both testing and validation image sets (Tables 1 and 3). In a prior study using a UV pulsed laser, detection of high concentration treatment sites using only red-band images was also found to be difficult.[17] However, when ratio images were constructed by dividing red-band images by corresponding blue-band images, detection of most 1:2 dilution contamination sites was successful. The results in this study using only Enhanced Range red-band images were superior to the results of the previous study when only red-band images were used for detection. Unfortunately, blue-band images were not available in this study due to the use of 417 nm excitation. Another advantage of the Extended Range image set was the enhanced ability to detect the 1:200 dilution treatment sites. Enhanced detection of this low concentration treatment was also seen for the High Range and the Midrange image sets.

The optimal situation might be to use UV excitation to allow acquisition of blue-band images for calculation of ratios for detection of high concentration contamination sites. However, using the Extended Range is also a viable option. Water baths are used commercially to remove apples from crates prior to processing, and apples are commonly brushed clean as they are removed from the water bath. We have demonstrated that the fluorescence responses of sites contaminated with high concentrations of feces are enhanced after the apples are washed and brushed.[17] In addition, use of the Extended Range for imaging offers the benefits of enhanced detection of low concentration contamination sites and a simple detection scheme, which consists of a linear mapping of intensities followed by a simple threshold.

The most successful detection scheme for Golden Delicious apples utilized the Short Range image set (Tables 2 and 4). The timing parameters for this image set were selected to meet two criteria, that the intensities for treated areas were greater than for untreated areas in red-band images, and that the reverse was true for corresponding yellow-band images. By analyzing both red-band images and ratios of red-band to yellow-band images, and by taking the union of detection results, it was possible to detect essential all of the 1:2 and 1:20 treatment sites for both 682 and 700 nm image sets; however, detection of 1:200 treatment sites was superior when the 700 nm image sets were analyzed. This is the only situation where images acquired at 700 nm appeared to produce better detection results compared to 682 nm. In any case, the most 1:200 dilution sites were detected when the High Range image set was analyzed. Still, current results are very good and the detection algorithms based on the Short Range timing parameters might prove useful in a commercial environment.

4. Conclusions

In this example, the use of time-resolved imaging allowed for the optimization of imaging parameters for the detection dairy feces artificially applied to apples. It was determined that fluorescence responses of untreated apple surfaces at 682, 700 and 732 nm attenuated to very low intensity levels faster with time (ns time-scale) then responses of areas treated with feces. At 590 nm, the shapes of responses for treated and untreated areas were similar. For Red Delicious apples, optimal detection of contamination sites utilized images acquired using the 682 nm filter with the camera exposure parameters set so the fluorescence response of the apple surface was largely gone but there was still some response from the areas treated with feces. For Golden Delicious apples, optimal detection utilized images acquired using the 682 and 590 nm filters, with the camera exposure parameters set so that images were taken during a time period where responses of treated areas exceeded responses of untreated areas in images acquired at 682 nm and responses were visible in images taken at 590 nm. Excellent overall detection resulted when both the 682 nm images and the ratio of the 682 to 590 nm images were analyzed and the detection results combined. These findings demonstrate that consideration of the timing of fluorescence responses to pulsed-laser excitation can enhance detection of feces on apples and can facilitate development of commercial systems to detect apples contaminated with feces.

It is understood that the foregoing detailed description is given merely by way of illustration and that modifications and variations may be made therein without departing from the spirit and scope of the invention.

References cited (the contents of each of which are incorporated by reference herein):
1. FDA, "Hazard analysis and critical control point (HAACP); Procedures for the safe and sanitary processing and importing of juices," Federal Registry 66, 6137-6202 (2001).
2. Food Safety Inspection Service, U.S. Department of Agriculture, "Verification of procedures for controlling fecal material, ingesta, and milk in slaughter operations," Directive 6420.2, http:www.fsis.usda.gov (2004), pp. 1-14.
3. G. L. Armstrong, J. Hollingsworth, and J. G. Morris Jr., "Emerging foodborne pathogens: *Escherichia coli* O157: H7 as a model of entry of a new pathogen into the food supply of the developed world," Epidemiol. Rev. 18, 29-51 (1996).
4. R. L. Buchanan and M. P. Doyle, "Foodborne disease significance of *Escherichia coli* 0157:H7 and other enterohemorrhagic *E. coli*," Food Technol. 51, 69-76 (1997).
5. R. E. Brackett, "Incidence, contributing factors, and control of bacterial pathogens in produce," Postharvest Biol. Tech. 15, 305-311 (1999).
6. P. S. Mead, L. Slutsker, V. Dietz, L. F. McCaig, J. S. Bresee, C. Shapiro, P. M. Griffin, and R. V. Tauxe, "Food-related illness and death in the United States," Emerging Infectious Diseases 5, 607-625 (1999).
7. Centers for Disease Control and Prevention, "Outbreaks of *Escherichia coli* 0157:H7 infection and cryptosporidiosis associated drinking unpasteurized apple cider-Connecticut and New York, October 1996," Morbid. Mortal. Weekly Rep. 46, 4-8 (1997).
8. P. J. Harris and R. D. Hartley, "Detection of bound ferulic acid in cell walls of the Gramineae by ultraviolet fluorescence microscopy," Nature 259, 508-510 (1976).
9. J. Hewett, V. Nadeau, J. Ferguson, H. Moseley, S. Ibbotson, J. W. Allen, W. Sibbett, and M. Padgett, "The application of a compact multispectral imaging system with integrated excitation source to in vivo monitoring of fluorescence during topical photodynamic therapy of superficial skin cancers," Photochem. Photobiol. 73, 278-282 (2001).
10. H. H. Kim, "New algae mapping technique by the use of an airborne laser fluoresensor," Applied Optics 12, 1454-1459 (1973).
11. V. Tassetti, A. Hajri, M. Sowinska, S. Evrard, F. Heisel, L. Q. Cheng, J. A. Mieh, J. Marescaux, and M. Aprahamian, "In vivo laser-induced fluorescence imaging of a rat pancreatic cancer with phosphorbide-a," Photochem. Photobiol. 65, 997-1006 (1997).
12. E. W. Chappelle, J. E. McMurtrey, and M. S. Kim, "Identification of the pigment responsible for the blue fluorescence band in laser-induced fluorescence (LIF) spectra of green plants, and the potential use of this band in remotely estimating rates of photosynthesis," Remote Sens. Environ. 36, 213-218 (1991).
13. M. S. Kim, A. M. Lefcourt, Y. R. Chen, I. Kim, K. Chao, and D. Chan, "Multispectral detection of fecal contamination on apples based on hyperspectral imagery. II. Application of fluorescence imaging," Trans. ASAE 45, 2027-2038 (2002).
14. D. Krizek, E. M. Middleton, R. Sandhu, and M. S. Kim, "Evaluating UV-B effects and EDU protection in cucumber leaves using fluorescence images and fluorescence emission spectra," J. Plant Physiol. 158, 41-53 (2001).
15. M. Sowinska, T. Decker, C. Eckert, F. Heisel, R. Valcke, and J. Miehe, "Evaluation of nitrogen fertilization effect on apple-tree leaves and fruit by fluorescence imaging," Proc. SPIE 3382: 100-111 (1998).
16. M. S. Kim, A. M. Lefcourt, and Y. R. Chen, "Optimal fluorescence excitation and emission bands for detection of fecal contamination," J. Food Protection 66, 1198-1207 (2003).
17. A. M. Lefcourt, M. S. Kim, and Y. R. Chen, "Automated detection of fecal contamination of apples by multispectral laser-induced fluorescence imaging," Applied Optics 42, 3935-3943 (2003).
18. M. S. Kim, A. M. Lefcourt, and Y. R. Chen, "Multispectral laser induced fluorescence imaging system for large biological samples," Applied Optics 42, 3927-3934 (2003).
19. A. R. Weeks Jr., Fundamentals of Electronic Image Processing (SPIE Optical Engineering Press, Bellington, Wash., 1996).
20. Kim et al., "Uses of hyperspectral and multispectral laser induced fluorescence imaging techniques for food safety inspection" Key Engineering Materials, vols. 270-273, pages 1055-1063 (2004).

TABLE 1

The number of Red Delicious apples from a total of 48 where the contamination site was successfully detected by filter (682 or 700 nm), treatment (1:2, 1:20 and 1:200 dilutions of dairy feces), and image set. Image sets relate to the gate timing of the ICCD camera. Algorithms used for detection were iteratively optimized for each image set.

|  | 682 nm | | | 700 nm | | |
|---|---|---|---|---|---|---|
| Gate Aperture | 1:2 | 1:20 | 1:200 | 1:2 | 1:20 | 1:200 |
| Low Range (3-27)[1] | 13 | 48 | 26 | 11 | 48 | 32 |
| High Range (15-34) | 31 | 48 | 46 | 22 | 48 | 46 |
| Mid-Range (12-19) | 26 | 48 | 45 | 23 | 48 | 46 |
| Short Range (11-13) | 16 | 48 | 33 | 14 | 48 | 40 |
| Ratio Short Range[2] | 4 | 27 | 18 | 4 | 34 | 35 |
| Extended Range (20-24) | 40 | 48 | 48 | 32 | 47 | 48 |

[1]Numbers in parentheses correspond to the window gate in ns.
[2]For ratio images, images in the indicated image set were divided by corresponding images acquired using the 590 nm filter.

TABLE 2

The number of Golden Delicious apples from a total of 48 where the contamination site was successfully detected by filter (682 or 700 nm), treatment (1:2, 1:20 and 1:200 dilutions of dairy feces), and image set. Image sets relate to the gate timing of the ICCD camera. Algorithms used for detection were iteratively optimized for each image set.

| | 682 nm | | | 700 nm | | |
|---|---|---|---|---|---|---|
| Gate Aperture | 1:2 | 1:20 | 1:200 | 1:2 | 1:20 | 1:200 |
| Low Range (3-27) | 36 | 46 | 32 | 31 | 46 | 34 |
| High Range (15-34) | 37 | 48 | 42 | 29 | 48 | 41 |
| Mid-Range (12-19) | 35 | 48 | 34 | 26 | 46 | 37 |
| Short Range (11-13) | 40 | 48 | 28 | 32 | 46 | 34 |
| Ratio Low Range | 46 | 46 | 18 | 43 | 47 | 26 |
| Ratio Short Range | 46 | 48 | 19 | 41 | 47 | 22 |
| Extended Range (20-24) | 31 | 44 | 38 | 21 | 41 | 36 |
| Combined Low Range[3] | 47 | 46 | 33 | 47 | 47 | 38 |
| Combined Short Range | 47 | 48 | 34 | 45 | 48 | 36 |

[1]Numbers in parentheses correspond to the window gate in ns.
[2]For ratio images, images in the indicated image set were divided by corresponding images acquired using the 590 nm filter.
[3]Results for combined image sets are the union of detection results for corresponding normal and ratio image sets.

TABLE 3

The number of Red Delicious apples from a total of 48 where the contamination site was successfully detected by filter (682 or 700 nm), treatment (1:2, 1:20 and 1:200 dilutions of dairy feces), and image set. Image sets relate to the gate timing of the ICCD camera. The optimized detection algorithms derived for Table 1 were applied to these image sets for validation.

| | 682 nm | | | 700 nm | | |
|---|---|---|---|---|---|---|
| Gate Aperture | 1:2 | 1:20 | 1:200 | 1:2 | 1:20 | 1:200 |
| Low Range (3-27)[1] | 10 | 47 | 22 | 5 | 46 | 31 |
| High Range (15-34) | 32 | 48 | 46 | 20 | 48 | 46 |
| Mid-Range (12-19) | 22 | 48 | 44 | 17 | 47 | 44 |
| Short Range (11-13) | 18 | 48 | 32 | 14 | 48 | 40 |
| Ratio Short Range[2] | 4 | 37 | 21 | 4 | 39 | 30 |
| Extended Range (20-24) | 40 | 48 | 47 | 29 | 47 | 48 |

[1]Numbers in parentheses correspond to the window gate in ns.
[2]For ratio images, images in the indicated image set were divided by corresponding images acquired using the 590 nm filter.

TABLE 4

The number of Golden Delicious apples from a total of 48 where the contamination site was successfully detected by filter (682 or 700 nm), treatment (1:2, 1:20 and 1:200 dilutions of dairy feces), and image set. Image sets relate to the gate timing of the ICCD camera. The optimized detection algorithms derived for Table 2 were applied to these image sets for validation.

| | 682 nm | | | 700 nm | | |
|---|---|---|---|---|---|---|
| Gate Aperture | 1:2 | 1:20 | 1:200 | 1:2 | 1:20 | 1:200 |
| Low Range (3-27)[1] | 35 | 46 | 24 | 29 | 47 | 27 |
| High Range (15-34) | 29 | 48 | 41 | 22 | 46 | 38 |
| Mid-Range (12-19) | 32 | 48 | 36 | 17 | 47 | 34 |
| Short Range (11-13) | 37 | 48 | 30 | 25 | 48 | 33 |
| Ratio Low Range[2] | 45 | 48 | 12 | 45 | 45 | 13 |
| Ratio Short Range | 45 | 45 | 13 | 36 | 47 | 16 |
| Extended Range (20-24) | 23 | 45 | 35 | 12 | 42 | 35 |
| Combined Low Range[3] | 46 | 46 | 24 | 45 | 48 | 36 |
| Combined Short Range | 46 | 48 | 30 | 47 | 47 | 38 |

[1]Numbers in parentheses correspond to the window gate in ns.
[2]For ratio images, images in the indicated image set were divided by corresponding images acquired using the 590 nm filter.
[3]Results for combined image sets are the union of detection results for corresponding normal and ratio image sets.

We claim:

1. A method for detecting fecal contamination on a surface of a fruit or vegetable which contains a native chlorophyll comprising:
   (a) illuminating the surface of a fruit or vegetable with a pulse of UV or visible light having a wavelength effective to elicit fluorescence of feces of an animal that directly or indirectly consumed plant products,
   (b) measuring the intensity of fluorescent light emissions from said surface at one or more wavelengths characteristic of the emission spectra of chlorophyll or chlorophyll degradation products, wherein said fluorescent light emissions are measured at a time period after the peak emission of the native chlorophyll of said fruit or vegetable, and
   (c) determining if said intensity of said fluorescent light emissions measured in (b) is significantly greater than a threshold value of the intensity of fluorescent light emissions for a non-feces contaminated control of the same fruit or vegetable measured at substantially the same conditions at substantially the same said time period and at substantially the same said wavelengths, wherein the determination that said intensity of said fluorescent light emissions measured in (b) is significantly greater than said threshold value is an indication of the presence of fecal material on said surface of said fruit or vegetable.

2. The method of claim 1, wherein said time period is after the peak emission of the native chlorophyll of said fruit or vegetable, and after the time at which at least about 50% of the energy of said fluorescent light emissions at said wavelengths has dissipated as measured in a fluorescence time decay curve.

3. The method of claim 1, wherein said time period after the peak emission of the native chlorophyll of said fruit or vegetable, is after the time at which about 50% of the energy of said fluorescent light emissions at said wavelengths has dissipated as measured in a fluorescence time decay curve.

4. The method of claim 1 wherein said measuring the intensity of fluorescent light emissions from said surface comprises a single measurement.

5. The method of claim 1 wherein said time period within about 30 nanoseconds after the peak emission of the native chlorophyll of said fruit or vegetable.

6. The method of claim 5 wherein said time period is between about 5 nanoseconds and about 30 nanoseconds after the peak emission of the native chlorophyll of said fruit or vegetable.

7. The method of claim 1 wherein said fruit or vegetable is selected from the group consisting of pome fruits, stone fruits, lettuce, melons, berries, and greens.

8. The method of claim 7 wherein said fruit or vegetable is selected from the group consisting of apples, pears, iceberg lettuce, romaine lettuce, cantaloupe, strawberries, collard greens, and spinach.

9. The method of claim 1 wherein said fluorescent light emissions are measured at a plurality of different, discrete positions on said surface of said fruit or vegetable.

10. The method of claim 9 further comprising determining any said position wherein said intensity of said fluorescent light emissions is significantly greater than said threshold value.

11. The method of claim 1 wherein said measuring of said fluorescent light emissions comprises acquiring a digital image of said fruits or vegetables.

12. The method of claim 11 wherein said fluorescent light emissions are measured at a plurality of discrete positions of said digital image, and said determining comprises determining any said position wherein said intensity of said fluorescent light emissions is significantly greater than said threshold value.

13. The method as described in claim 1 further comprising transporting said fruits or vegetables on a conveyor line, and further wherein said illuminating, measuring, and determining are conducted while said fruits or vegetables are transported on said conveyor line.

14. The method of claim 1 further comprising removing said fruits or vegetables from said conveyor line if said intensity of said fluorescent light emissions is significantly greater than said threshold value.

15. The method of claim 1 further comprising washing or decontaminating said fruits or vegetables if said intensity of said fluorescent light emissions is significantly greater than said threshold value.

16. The method of claim 1 wherein said illuminating comprises illuminating said surface with light having a wavelength between about 280 to about 670 nm.

17. The method of claim 16 wherein said illuminating comprises illuminating said surface with light having a wavelength between about 410 to about 430 nm.

18. The method of claim 1 wherein said measuring comprises measuring the intensity of fluorescent light emissions from said surface at one or more wavelengths between about 600 to about 760 nm.

19. The method of claim 1 wherein said measuring comprises measuring the intensity of fluorescent light emissions from said surface at one or more wavelengths between about 650 to about 700 nm.

* * * * *